United States Patent [19]

Aizu et al.

[11] Patent Number: 4,743,107
[45] Date of Patent: May 10, 1988

[54] OPHTHALMOLOGICAL DIAGNOSIS METHOD AND APPARATUS

[75] Inventors: Yoshihisa Aizu, Machida; Kouji Ogino, Hino, both of Japan

[73] Assignee: Kowa Company Ltd., Aichi, Japan

[21] Appl. No.: 16,285

[22] Filed: Feb. 19, 1987

[30] Foreign Application Priority Data

Feb. 25, 1986 [JP] Japan .................................. 61-38240
Mar. 27, 1986 [JP] Japan .................................. 61-67339

[51] Int. Cl.$^4$ ........................ A61B 3/10; A61B 5/02; G01P 3/36
[52] U.S. Cl. .................................. 351/221; 351/211; 351/206; 128/691; 356/28.5
[58] Field of Search ............... 351/205, 206, 207, 211, 351/213, 214, 221; 128/303.1, 691; 356/28, 28.5

[56] References Cited

U.S. PATENT DOCUMENTS

| | | | |
|---|---|---|---|
| 4,311,383 | 1/1982 | Ohtsubo ............................ | 356/28.5 |
| 4,346,991 | 8/1982 | Gardner et al. ..................... | 351/221 |
| 4,402,601 | 9/1983 | Riva ................................ | 351/221 |

*Primary Examiner*—John K. Corbin
*Assistant Examiner*—P. M. Dzierzynski
*Attorney, Agent, or Firm*—Bruce L. Adams; Van C. Wilks

[57] ABSTRACT

An ophthalmological diagnosis method and an apparatus for carrying out the method are disclosed. According to the method a region of the eye, e.g. the fundus, is illuminated with a laser beam of prescribed diameter to produce a laser speckle pattern formed by light scattered by blood cells within the tissue of the eye, movement of the laser speckle pattern is detected as fluctuation in the light intensity of the speckles at an observation point and a speckle signal corresponding to the detected movement is produced, the power spectrum distribution of the speckle signal is obtained, the power spectrum distribution configuration is evaluated from the results of a calculation of the mean frequency thereof and the blood flow state in the tissue is determined from the results of the evaluation. The apparatus for carrying out this method comprises a laser beam source, a laser beam optical system for guiding laser light from the laser beam source, adjusting it to a predetermined beam diameter and causing it to illuminate a region of eye tissue of predetermined area, means for measuring light scattered from the illuminated region of eye tissue and producing a signal corresponding to the result of the measurement, and means for processing the signal from the measuring means.

46 Claims, 13 Drawing Sheets

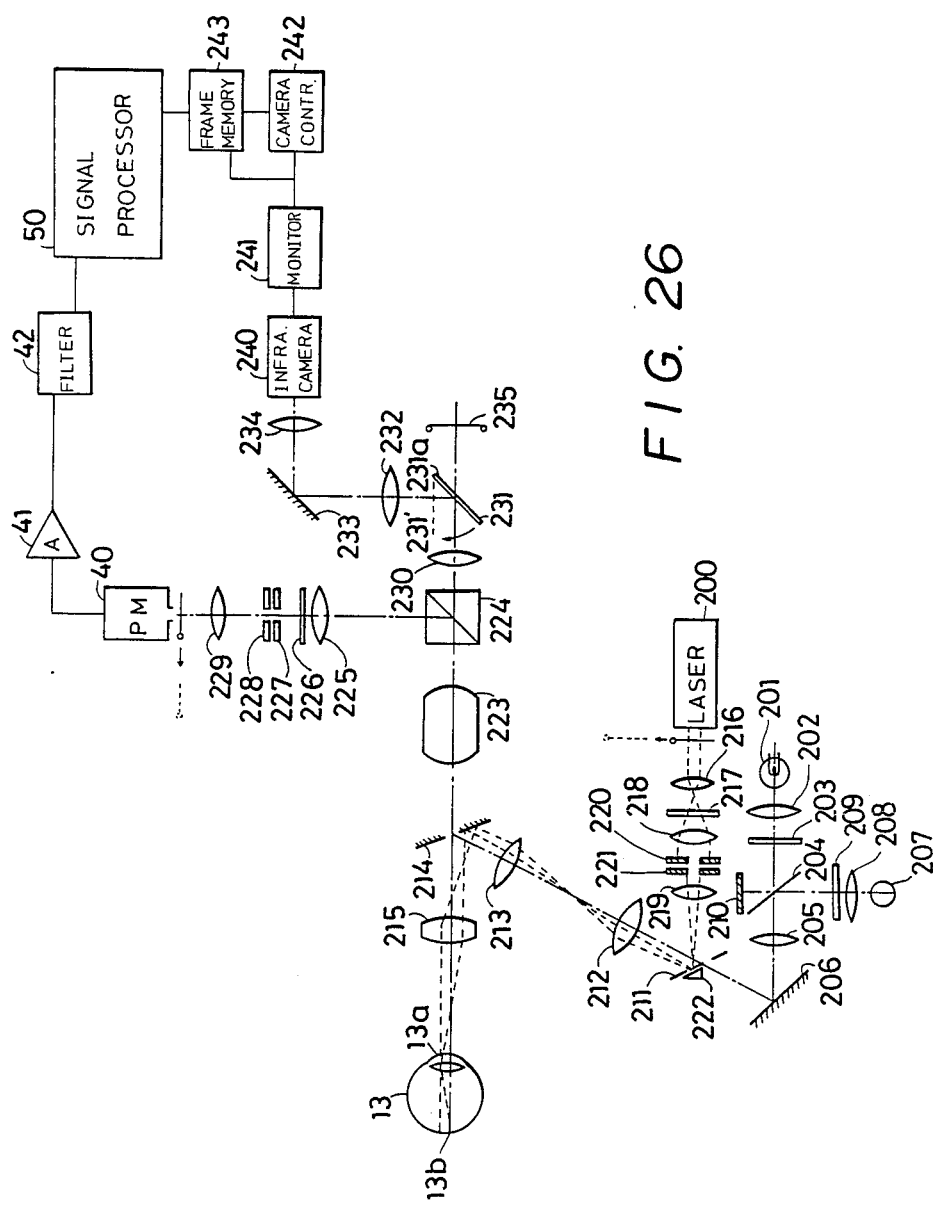
F I G. 26

OPHTHALMOLOGICAL DIAGNOSIS METHOD AND APPARATUS

BACKGROUND OF THE INVENTION

1. Field of the Invention

This invention relates to an ophthalmological diagnosis method and an apparatus for carrying out this method, more particularly to an opthalmological diagnosis method and apparatus which use the laser speckle phenomenon for measuring the state of blood flow in the tissue of the eye fundus, the iris and other regions falling within the scope of ophthalmology.

2. Description of the Prior Art

It is known that when a laser beam strikes an object which causes diffusion or scattering of the beam, the light scattered from the body generally gives rise to a speckle pattern caused by interference between reflected rays of the coherent light. In this case, any movement of the body causing the scattering will cause movement of the speckle pattern which can be detected as a time-course change in light intensity at an observation point. Thus, if the changes in intensity are converted into a signal, it becomes possible to measure the movement of the light-scattering body from the signals. The present invention applies this principle to the measurement of the state of blood flow in living tissue such as, for example, the tissue constituting the eye fundus.

One conventional method for measuring blood flow in the eye fundus is the laser-Doppler method described in Applied Optics (Optical Society of America), Vol. 20, No. 1 (January, 1981), pp 117–120. In this method, a laser beam is directed onto the blood vessels of the eye fundus using an eye fundus camera and the frequency shift of the laser light caused by the Doppler effect when the light is scattered by the blood cells flowing through the blood vessels (this shift being proportional to the velocity of the blood cells) is measured and used for calculating the blood flow velocity.

For the detection of the Doppler frequency shift required by this method there are only two possible arrangements. One is split the laser beam into two beams forming equal angles with respect to the optical axis of the original laser beam and to direct the split beams into the eye to be examined such that they intersect precisely at the position of the eye fundus blood vessel concerned. The other is to direct a single laser beam onto the eye fundus blood vessel and to detect the laser light scattered by the blood cells from two different directions. In either case, the required optical system is complex and must be of high precision. Moreover, the fact that the angle of beam incidence or light detection has to be known in advance, the fact that a laser beam adjusted to a beam diameter substantially equal to the diameter of the blood vessel concerned (generally between several tens of $\mu m$ and several hundred $\mu m$) has to be directed onto the blood vessel with high precision, and the fact that the person being subjected to the examination has to be kept stationary during the period of measurement both make this method extremely difficult to apply clinically and greatly impair the repeatability and reliability of the results it produces.

Further, in actual measurements the results are not obtained as a asingle Doppler shift frequency but consist of wide-ranging frequency components extending from the low frequency side to the high frequency side, making it difficult to obtain a reliable absolute velocity value.

Other problems arise from the fact that the laser beam can be directed onto the eye fundus only along paths that are perpendicular or nearly perpendicular to the eye fundus. At such angles, the Doppler shift is very small and the beat signals are hard to detect. This is because the laser Doppler method requires the detection of a single beat component. Thus in applications relating to biological tissues, which produce a wide range of irregular interferences, it is preferable to make use of the laser speckle method, the very essence of which is the interference effect of irregularly scattered light.

As prior art references related to blood flowmeters employing the laser speckle principle there can be mentioned Japanese Unexamined Patent Publication Nos. 60(1985)-199430, 60(1985)-203235 and 60(1985)-203236. The operating principle of the inventions described in these publications is to direct laser light onto the surface of a biological tissue though an optical fiber, to guide the light scattered by the blood cells under the surface of the tissue through another optical fiber to a photomultiplier tube and then either to output a voltage proportional to the frequency of the so-detected speckle signal or to determine the frequency gradient of the speckle signal, in this way measuring the state of blood flow.

While blood flowmeters of this type can be applied to the skin and other biological tissue that enable easy laser light irradiation and detection, they are hard to apply in the field of ophthalmology which deals with a special biological structure that itself constitutes an optical system.

Moreover, for directing the laser light onto the region where the measurement is to be made, these meters require the use of a special probe fitted at the end of the optical fiber. The shape of this probe is such that it prevents accurate observation of the state and location of the region which is actually being illuminated with laser light from the optical fiber within the probe. Further, since the light issuing from the optical fiber spreads with increasing distance from the fiber tip, it is necessary to bring the tip of the fiber near the biological tissue under observation, which is difficult to accomplish in carrying out blood flow measurement in the field of ophthalmology.

SUMMARY OF THE INVENTION

It is therefore an object of the invention to provide an ophthalmological diagnosis method and apparatus enabling accurate and effective measurement of the state of blood flow in tissues falling within the scope of ophthalmological examination, using the laser speckle phenomenon.

The present invention realizes this object by providing an arrangement wherein a laser beam of predetermined diameter is directed toward the eye, the movement of a speckle pattern formed by light scattered by blood cells within the eye tissue is detected as fluctuation in speckle light intensity at an observation point, and the state of blood flow within the tissue is determined by evaluating the results obtained by subjecting the configuration of the power spectrum distribution of the so-obtained speckle signal to mean frequency calculation.

Rather than providing a measurement of the absolute velocity of blood flowing through a specific single blood vessel, this arrangement enables an overall, averaged evaluation of the state of blood flow in a plurality of blood vessels included within the irradiated region of the eye and as such enhances the operability of the apparatus used for the measurement while also increasing the reliability and consistency of the measured results.

The present invention provides numerous advantageous effects. For example, (1) Since the principle involved is that of detecting the intensity fluctuation of the laser speckles and then processing the so-obtained signals to obtain movement information regarding light-scattering bodies (blood cells), it is sufficient to detect the light scattered by the blood cells in the blood vessel being examined at the plane of observation, meaning that the optical system can be very simple and the entire apparatus easy to fabricate.

(2) As the region over which the state of blood flow can be measured is broader than in conventional methods, the effect caused by slight movements of the eye under examination while the measurement is being carried out is smaller than heretofore.

(3) In the signal processing, as the evaluation of the state of blood flow is made not with respect to only a part of the power spectrum of the speckle signal but with respect to the configuration of the entire power spectrum, the accuracy of the measurement is high.

BRIEF DESCRIPTION OF THE DRAWINGS

The objects and features of the present invention will become more apparent from a consideration of the following detailed description taken in conjunction with the accompanying drawings in which:

FIG. 26 is a schematic view of another embodiment of an optical system;

DETAILED DESCRIPTION OF THE PREFERRED EMBODIMENTS

The invention will now be described in detail with reference to the drawings.

While the embodiments described in the following relate to the application of the invention to ophthalmological diagnosis involving the use of an eye fundus camera to measure blood flow in the tissue of the eye fundus, the invention is not limited to such application and can be applied in a wide range of other forms of ophthalmological examination as well.

Figure 1:
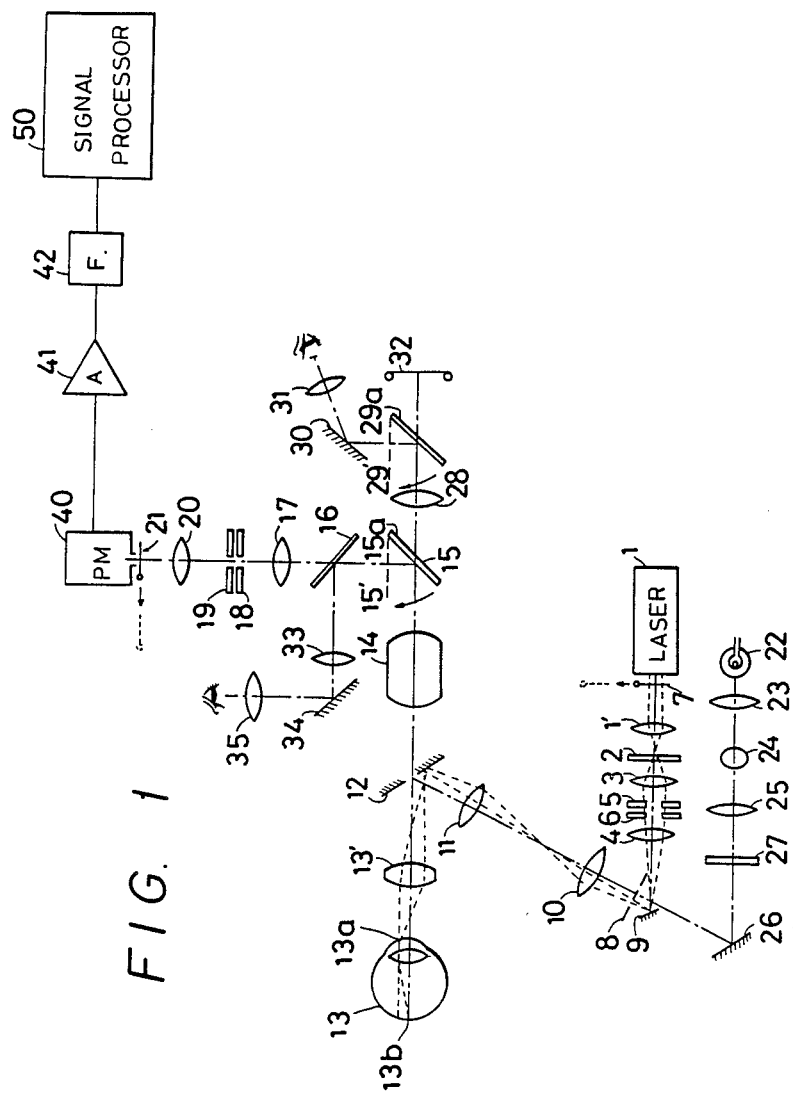
FIG. 1 is a diagram showing the structure of a first embodiment of the apparatus according to the present invention.
Figure 2:
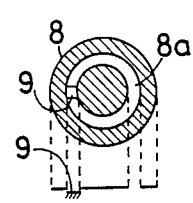
FIG. 2 is a diagram for explaining the structure of a ring slit.

FIG. 1 shows an overall schematic view of an apparatus for carrying out the measurement method according to the present invention. A laser beam from a He-Ne, argon or other type laser beam source 1 is passed through a condenser lens 1', and then through a light quantity adjustment filter 2 for adjusting the intensity of the beam. Thereafter the beam is passed through relay lenses 3 and 4 and introduced into the eye fundus illuminating projector of an eye fundus camera. A pair of stops 5 and 6 are disposed between the relay lenses 3 and 4 for selectively adjusting the size and shape of the region of the eye fundus irradiated by the laser beam and a shutter 7 is disposed near the beam-emitting end of the laser beam source 1 to enable the beam to be cut off or passed as required. As shown in FIG. 2, the laser beam emitting from the relay lens 4 is reflected by a mirror 9 provided in one portion of an annular aperture 8a formed in a ring slit 8 constituting a part of the eye fundus illuminating projector, whereafter the reflected laser beam travels along the same light path leading to the eye fundus under examination as that followed by a beam of light directed onto the eye fundus for providing illumination for photographic observation. As a result, the laser beam passes through relay lenses 10 and 11, is reflected by a ring mirror 12, is converged on the cornea 13a of the eye under examination 13 by an objective lens 13' and then diverges as it advances toward the eye fundus 13b where it illuminates a region which is larger than the diameter of the individual blood vessels of the type referred to earlier.

This illuminated area is also illuminated by the illuminating projector of the fundus camera so as to facilitate observation. The system for providing the illumination for observation is constituted of an observation light source 22 disposed on the same light path as a photographic light source 24, a condenser lens 23, a condenser lens 25, a filter 27 and a mirror 26. As the path of the laser beam coincides with that of the beam of observation light, the laser beam can be made to impinge on the desired region of the eye fundus 13b by use of the mechanisms for swinging the eye fundus camera vertically and horizontally and also by use of the eye fixation mechanism.

Figure 3:
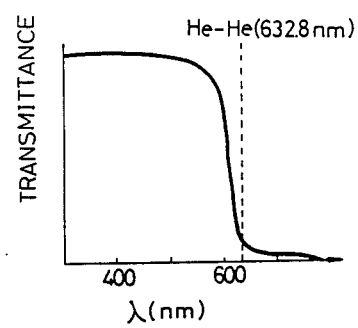
FIG. 3 is a characteristic curve showing the characteristics of a wavelength separation filter used in the embodiment of FIG. 1.

The filter 27 disposed between the condenser lens 25 and the mirror 26 is a wavelength separation filter which, exhibiting characteristics as shown in FIG. 3, cuts out red components from the observation and photographic light.

The speckle light arising when the laser beam is scattered by the blood cells moving through the blood vessels in the eye fundus enters the objective lens 13', passes through the ring mirror 12 and then proceeds through a photographic lens 14 and a wavelength separation mirror 15. Similarly to the filter 27, the wavelength separation mirror 15 also exhibits spectral characteristics as illustrated by FIG. 3 and, therefore, since it reflects almost all light of wavelengths not shorter than the red band and passes all lower wavelength light, it reflects most of the speckle light (red) generated by the He-Ne laser beam. The reflected light advances through a beam splitter 16, a relay lens 17 and detection apertures 18 and 19, whereafter it is converged once again by a condenser lens 20 and sent into a photomultiplier 40 for detection. A shutter 21 is disposed in front of the photomultiplier 40 and the signal produced by the photomultiplier 40 at the time this shutter is open is sent to through an amplifier 41 and a filter 42 to a signal processor 50.

Figure 4:
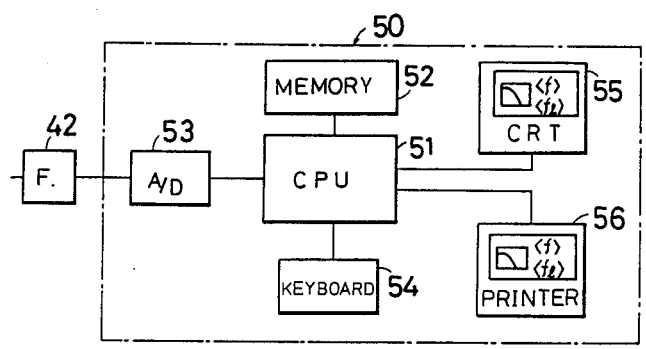
FIG. 4 is a block diagram of a single processor used in the embodiment of FIG. 1.

As shown in FIG. 4, the signal processor 50 is constituted of a CPU (central processing unit) 51, a memory 52, an A/D (analog/digital) converter 53, a keyboard 54, a CRT (cathode ray tube) display 55 and a printer 56.

The light passing through the wavelength separation mirror 15 advances through a relay lens 28, is reflected by a swingable mirror 29 and a mirror 30 and proceeds to an eyepiece 31 through which it can be observed by the operator. Alternatively, when the swingable mirror 29 is raised, the light can be recorded on a photographic film 32.

Further, a part of the speckle light reflected by the beam splitter 16 passes through a relay lens 33 and is reflected by a mirror 34 to an eyepiece 35 through which the operator can observe the speckle pattern.

The operation of the apparatus according to the invention shown in FIG. 1 will now be explained with reference to the flowcharts of FIGS. 5 and 6.

Figure 5:
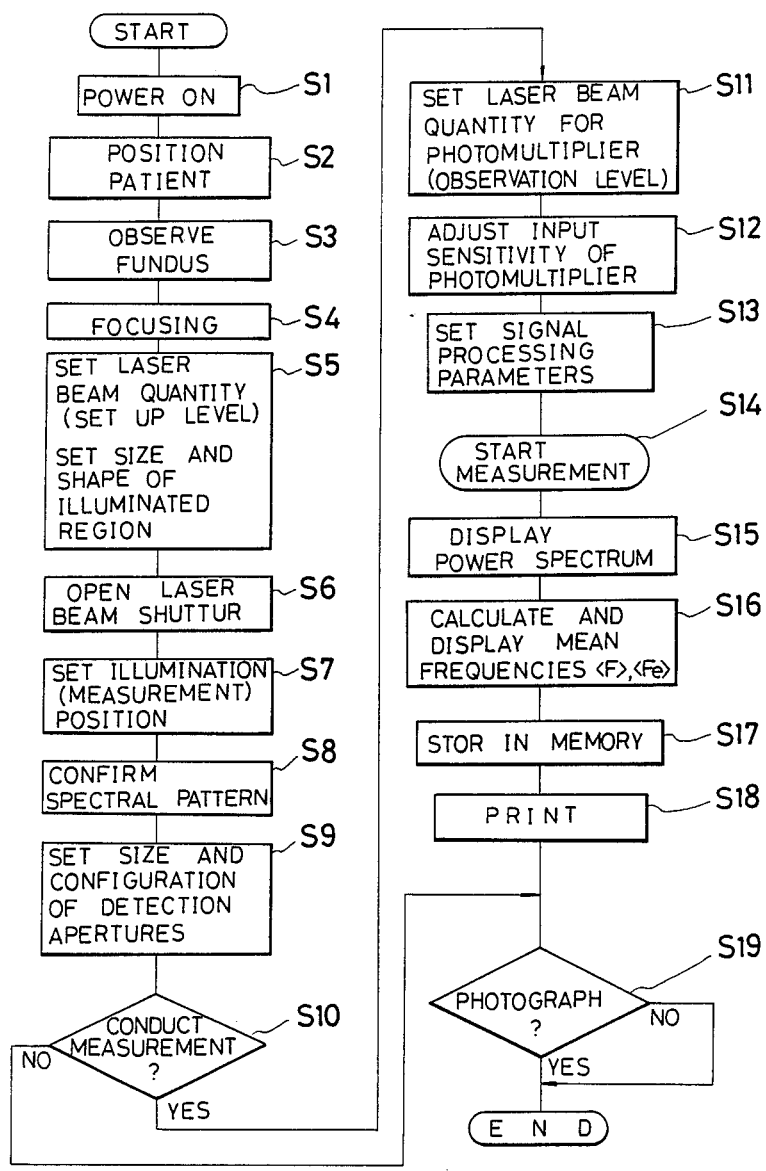
FIGS. 5 and 6 are flowcharts showing the flow of control processes.

In the flowchart of FIG. 5, after the power has been turned on in step S1, the patient positioned in step S2 and the eye fundus 13b of the eye 13 under examination is observed in step S3 using light from the observation light optical system constituted by the optical elements 22 to 26. Then, following focusing in step S4, the laser light beam source 1 is activated in step S5. At this time, the filter 2 is used to adjust the quantity of light to the level for system set-up and the stops 5 and 6 are used to set the size and shape of the region illuminated by the laser beam. The procedure then moves to step S6 in which the shutter 7 is opened and to steps S7 and S8 in which the measurement position is set and the speckle pattern is confirmed. The size and shape of the apertures 18 and 19 is then set in step S9, whereafter, if measurement is to be conducted, the laser output is adjusted to the measurement level, the shutter 21 of the photomultiplier 40 is opened and the sensitivity of the photomultiplier 40 to input is adjusted (steps S10 to S12). Then the signal processing parameters are set in step S13 and measurement is begun in step S14.

The output produced by the photomultiplier 40 during measurement constitutes a speckle signal which varies with time in accordance with the movement of the blood cells. This speckle signal is amplified by the amplifier 41 whereafter, if necessary, it is passed through the band pass filter 42 whose band is set so as to remove unnecessary frequency components. The speckle signal is then input to the signal processor 50 (a microcomputer) where, as shown in FIG. 4, it is first converted into digital form by the A/D converter 53 and then processed to obtain the power spectrum distribution. For this, the signal processor executes an analysis program prepared in advance. The result is once displayed as a distribution configuration on the display 55 (step S15). As the rate of fluctuation in speckle light intensity changes in proportion to the velocity of the blood cells, the power spectrum of the speckle signal extends toward the high frequency side when the blood cell velocity is high. To the contrary, it consists mainly of low frequency components when the cell velocity is low.

Figure 7A:
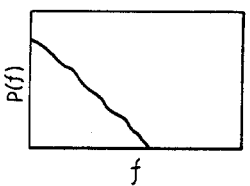
FIGS. 7(a)-7(e) are graphs for explaining power spectrum distributions.
Figure 7B:
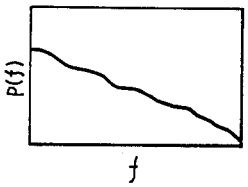
Figure 7C:
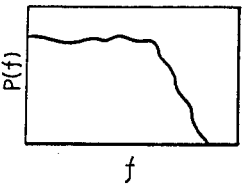
Figure 7D:
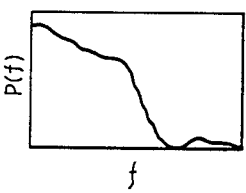
Figure 7E:
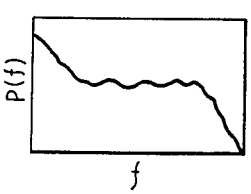

As a means of evaluating the power spectrum there is known a method involving determination of the frequency gradient. While this prior art method can be applied to relatively simple distributions as shown in FIGS. 7(a) and (b), it does not work well in situations such as shown in FIGS. 7(c) to (e) where, because of the need to focus on a specific region of the power spectrum, it is difficult to make an evaluation solely on the basis of frequency gradient. Unlike the prior art, the present invention also takes into consideration the possibility of complex power spectrum distribution and for this adopts a general mean frequency $<f>$ as defined by the following equation:

$$<f> = \frac{\int_0^\infty fP(f)df}{\int_0^\infty P(f)df}$$

where f denotes frequency and P(f) the power spectrum.

Further, in order to more strongly emphasize differences in the power spectrum distribution configuration, a parallel computation is carried out to determine a mean frequency $<fe>$ using the logarithm of hte power spectrum, as follows:

$$<fe> = \frac{\int_0^\infty f\{\log_{10}P(f) - \log_{10}P(f)min\}df}{\int_0^\infty \{\log_{10}P(f) - \log_{10}P(f)min\}df}$$

where $\log_{10}P(f)min$ is logarithm of the minimum value of P(f) in the data concerned.

Figure 6:
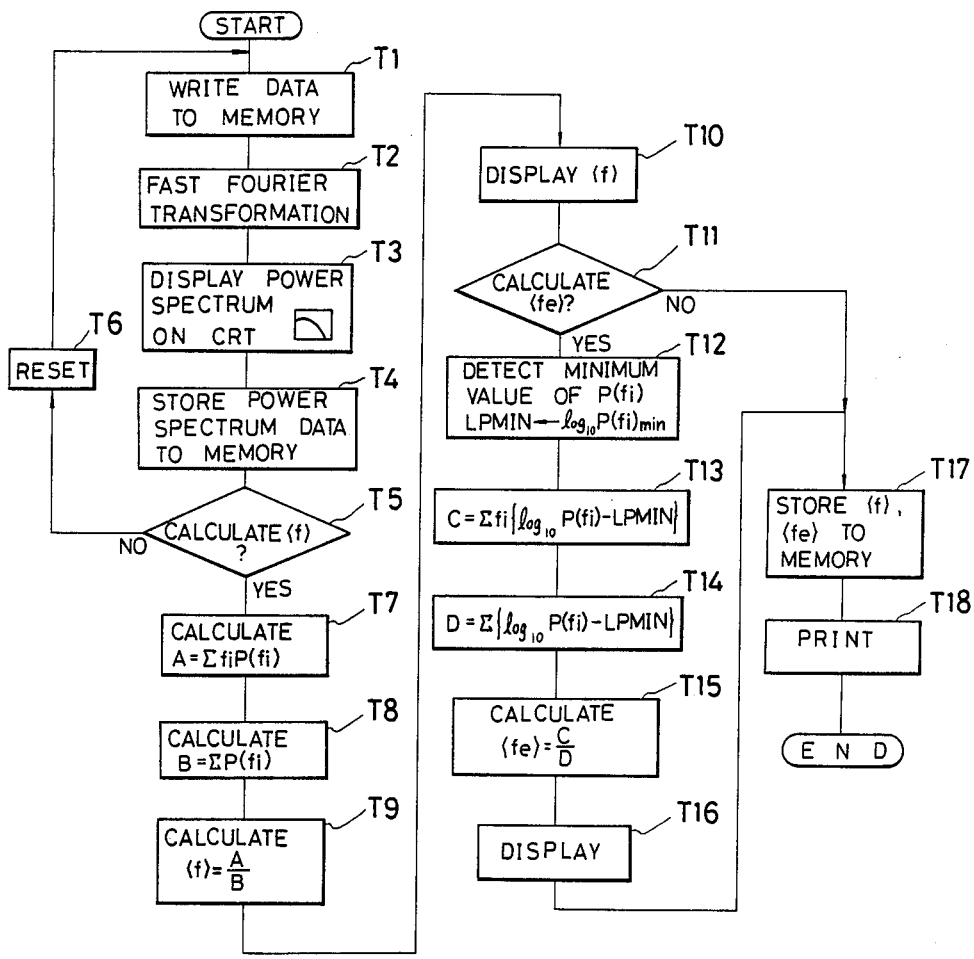

The calculation of $<f>$ and $<fe>$ is carried out in accordance with the flowchart shown in FIG. 6. In steps T1 to T4 the data is written into memory 52, fast Fourier transformation is carried out under the control of the CPU 51, the power spectrum is displayed on the CRT display 55 and the power spectrum data is stored in memory 52. In step T5 it is decided whether or not to calculate $<f>$ and if the decision is YES, the procedure continues through T7 to T10 in which $<f>$ is calculated anad displayed on the CRT display 55. If the decision is NO in step T5, the procedure is reset in step T6 and returns to step T1.

Then in step 11 it is decided whether or not to calculate $<fe>$. If the decision is YES, the calculation is carried out in steps T12–T15 and the so-obtained $<fe>$ is displayed on the CRT display 55 in step 16 and stored in memory 52 in step T17. When it is decided in step T11 not to calculate $<fe>$, $<f>$ is stored in memory 52 in step T17. In either case, the calculated data is also printed out in step T18 by the printer 56.

Returning to FIG. 5, it is decided instep S19 whether or not ot photograph the output results.

As the calculated mean frequencies $<f>$ and $<fe>$ will be higher when the power spectrum includes more components on the high frequency side and will be lower in the opposite case, the state of blood flow can be determined from the calculated results. As the calculation of $<f>$ and $<fe>$ is normalized for the full power amount, it is not affected by changes in the aggregate light intensity during measurement. As the signal processing explained above can be carried out in a relatively short time, it becomes possible to observe the measured state of blood flow substantially in real time. Moreover, as the power spectrum information for the entire region is reflected in the calculation, the measurement of the blood flow state can be conducted with high consistency.

In the present invention, at the portion of the eye being subjected to measurement, the region illuminated by the laser beam is set to be larger than a single blood vessel, i.e. is set to a diameter of, say, 1–3 mm, so that a plurality of blood vessels are included within the illuminated region. As a result, both the conventional requirement to adjust the illuminating laser beam to a small beam diameter approximating that of a specific single blood vessel and that of splitting the laser beam into two beams are eliminated, making it much easier to carry out the laser beam illumination. Another advantage is that moderate degrees of movement of the eye 13 during the examination will not have an appreciable effect on the results of the measurement. More specifically, even if there should be some shift of the illuminated region caused by a shift in the measurement position (i.e. by eye movement), the area newly included within the illuminated region because of this shift will be small in comparison to the portion of the previously illuminated area that still remains illuminated so that the speckle light from the blood vessel portions moving in and out of the illuminated region will have little effect on the intensity fluctuation of the overall speckle light scattered by the illuminated tissue region as a whole. As a consequence, the measurement region can be presumed to be substantially equivalent to a fixed region.

The invention is also free of any requirement of picking up the scattered light from a plurality of different angles and enables measurement to be carried out irrespective of the angle of light incidence of angle of light reception, wherein it becomes possible to obtain results with excellent repeatability and reliability. This is one of the main features of the present invention. The basic principle of the method according to this invention is not to measure the absolute blood flow velocity within a single blood vessel but to evaluate the overall, average state of blood flow within a plurality of blood vessels encompassed by the illuminated region. In other words, by detecting the intensity fluctuation in a speckle pattern affected by all bodies causing light scattering within a large region of laser beam illumination, the method enables measurement of the individual blood flow states within the region illumintaed by the laser beam in terms of the aggregate mean state thereof. This method of measuring the state of blood flow in terms of an aggregate mean value is essentially different from any other blood flow measurement method used heretofore in ophthalmological diagnosis. By the adoption of this method, the present invention enables the measurement to be carried out with greater ease and with an improvement in both the reliability and stability of the results obtained. Because of its ability to provide an overall evaluation of the state of blood flow, the method of the present invention exhibits especially outstanding effect in the measurement of blood flow through small-diameter blood vessels such as the capillaries.

Figures 8A, 8B:
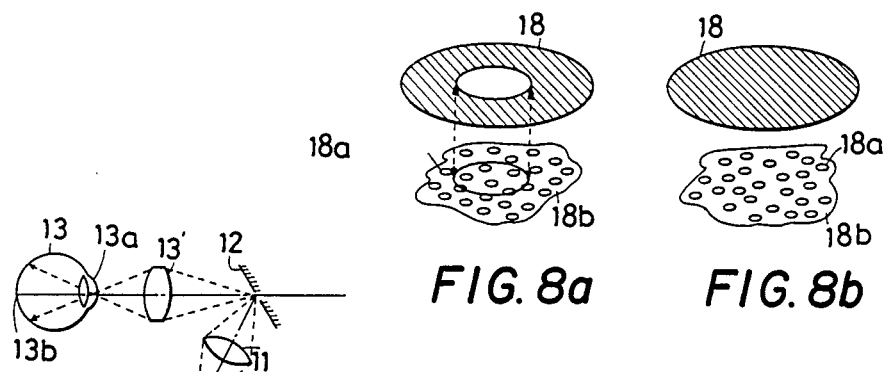
FIGS. 8(a)-8(b) are perspective views for explaining the relationship between a detection aperture and the speckle pattern.

It should be noted, however, that it is undesirable to expand the region of illumination beyond what is actually necessary. One reason for this is that an excessive large region of illumination makes it difficult in actual practice to independently illuminate portions having particular types of blood vessels such as at and in the vicinity of the papilla. Another is that the speckles formed at the detection apertures 18 and 19 become exceedingly small, making good quality extraction of the light intensity fluctuation impossible. The size of the speckles depends not only on the diameter of the region illuminated by the laser beam but also on the diamter of the pupil of the eye under examination. If the diameters of the detection apertures 18 and 19 are too large in comparison with the diameter of the speckles, a large number of speckles 18a will be integrated within the aperture area as shown in FIG. 8(a), making it impossible to extract the fluctuation in light intensity caused by the individual speckles. On the other hand, if these diameters are too small, then, as shown in FIG. 8(b), measurement becomes altogether impossible because the amount of received light becomes inadequate. Some examples of an appropriate combination of illuminated region diameter and aperture diameter would be 3 mm for the former and 50 um for the latter, or 1 mm for the former and 70–100 um for the latter. The need for selecting such an appropriate combination derives from the basic nature of the laser speckle phenomenon, namely that the diameter of the speckles at the plane of observation always varies with the diameter of the illuminated region.

While the speckle pattern obtained from the eye fundus 13b is observed at a conjugate image plate with respect to the eye fundus, since in the present invention the light scattered by the entirety of the region illuminated by the laser beam contributes to the detection, the basic principle involved is that of carrying out the detection of speckle light with the detecting apertures positioned at the Fraunhofer diffraction plane with respect to the eye fundus 13. In this respect, it is well known that a single spot of light at the Fraunhofer diffraction plane consists of superposed rays of light scattered from the respective spots within the illuminated region.

Figure 9:
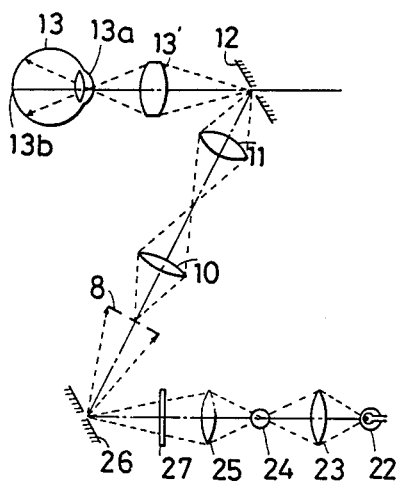
FIG. 9 is a schematic view of an optical system for visual and photographic observation.

The apparatus according to this invention can be arranged to carry out measurement of blood flow while also functioning as an eye fundus camera. In such case, the light from the observation light source 22 in FIG. 1 follows the beam path shown in FIG. 9. Namely, it advances through the condenser lens 23, the photographic light source 24, the condenser lens 25, whereafter it is reflected by the mirror 26 and, passing through a conventional fundus camera illuminating projector, illuminates the eye fundus 13b.

Figure 10:
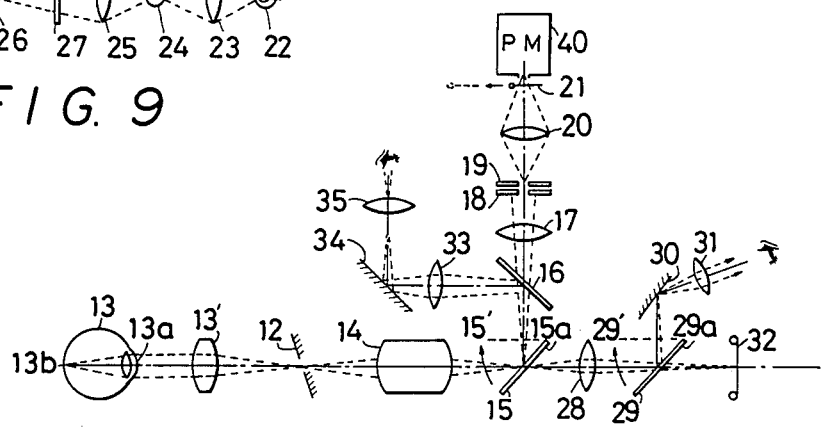
FIG. 10 is a schematic view of an optical system for carrying out measurement.

Further, as will be noted from the embodiment illustratèd in FIG. 1, a wavelength separation filter 27 possessing the spectral characteristics shown in FIG. 3 is disposed between the condenser lens 25 and the mirror 26. Thus, since the red light components contained in the observation and photographic light are cut, the red light reflected by the wavelength separation mirror 15 and detected by the photomultiplier 40 is limited solely to the that from the laser beam used for measurement. The light from the observation and photographic light sources thus have no effect on the speckle light. As best seen in FIG. 10, the observation light which transmits through the wavelength separation mirror 15 advances through the relay lens 28, is reflected by the swingable mirror 29 and the mirror 30, and then enters the eyepiece 31 through which it can be observed by the operator at the same time that the measurement is being carried out. Alternatively, if desired, the photographic light passing through the wavelength separation mirror 15 can be directed to and photographed on the photographic film 32. In this case, the swingable mirror is raised to the position indicated by the reference numeral 29' by swinging it about its hinge 29a in the direction indicated by the arrow. Since as shown in FIG. 3, the wavelength separation mirror 15 will pass a small amount of the red light of the laser beam, the position at which the eye fundus 13b is illuminated by the laser beam can be directly observed visually or be recorded photographically, a system which exhibits good effect as regards recording of the measurement results. In view of the fact that it might also be desired to employ the apparatus simply as an ordinary eye fundus camera, the wavelength separation mirror 15 is arranged so that it can be raised to and fixed at the position indicated by the reference numeral 15' by swinging it about its hinge 15a in the direction indicated by the arrow.

When the embodiment illustrated in FIG. 1 is used as a fundus camera, it can, by adjusting the diopter of the photographic lens 14, be used in the ordinary way to observe and photograph the forward portion of the eye. Taking advantage of this feature, the apparatus can be used without modification for the measurement of the state of blood flow in the forward region of the eye in the same manner as described above for such measurement at the eye fundus. It is thus possible to apply the apparatus for measurements at portions such as the iris and sclera where the blood vessels lie relatively close to the surface. Almost no practical equipment has heretofore been available for measurement of the state of blood flow in the iris etc. and the significance of the invention is particularly great in the sense that it can be applied to considerable advantage in diagnosis and examination conducted on the forward portion of the eye to determine the state of illness, the effect of medicinal treatment and the results of surgery. Further, another key feature of the invention is the high utility in clinical applications deriving from its ability to enable the blood flow states at different portions of the eye such as the eye fundus and iris to be measured and compared under identical conditions.

As regards the flowchart of FIG. 5, it should be noted that the procedure can alternatively be started after those settings known beforehand have been made. For example, it may be possible to set in advance the laser beam quantity (S5), the size and shape of the laser beam (S5), the size and configuration of the detection apertures 18 and 19 (S9), the signal processing parameters (S13) and the like. Moreover, photographic recording is by no means limited to the final stage of the examination but can be carried out under various conditions at arbitrarily selected times. The power spectrum and the mean frequencies $<f>$ and $<fe>$ can be printed out in full or selectively.

While one fundamental embodiment of the invention has been described in the foregoing, a wide range of variations and improvements are also possible. Some examples will be described in the following.

Figure 11:
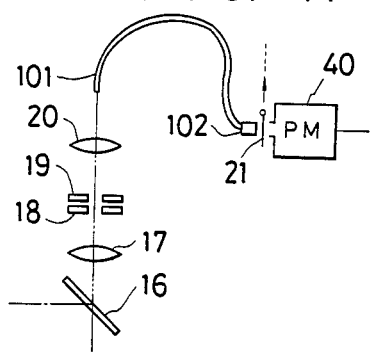
FIG. 11 is a schematic view of another embodiment of an optical system for carrying out measurement.

In the embodiment illustrated in FIG. 11, the light passing through the detecting apertures 18 and 19 and converged by the condenser lens 20, i.e. the light to be subjected to speckle detection, is directed into the light receiving end of an optical fiber 101 and the light exiting from the other end thereof is directed into the photomultiplier 40 thorugh a lens 102. This arrangement makes it possible to separate the photodetector from the main unit of the apparatus and thus enables simplification of the main unit structure. This embodiment also enjoys enhanced mechanical stability.

Figure 12:
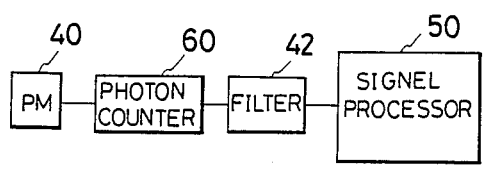
FIGS. 12 and 13 are a block diagram and a flowchart showing another method of measurement.

In the embodiment shown in FIG. 12, the speckle light output by the fundamental embodiment and detected by the photomultiplier 40 is forwarded to a photon counting unit 60 where a photon count is conducted. The output of the photon counting unit 60 is sent through a filter 42 to the signal processor 50 in order to obtain a photon correlation output. As in the correlation curve obtained from the photon correlation output the correlation length becomes shorter (longer) when the blood flow is faster (slower), the state of blood flow can be determined from the correlation length. The correlation output is obtained through a calculation carried out in accordance with a program like, for example, the one illustrated by the flowchart of FIG. 13. The program used is substantially the same as that represented by the flowchart of FIG. 6, the difference being that in steps R1 to R4 the photon correlation output is calculated instead of the power spectrum.

This photon correlation method is highly precise and can be effectively used even in cases where the intensity of the laser speckle light is so extremely weak as to make use of the signal processing method of FIG. 6 impossible.

When detection is carried out using light passed though an optical fiber as in the embodiment of FIG. 11, it is generally preferable to use a single mode type optical fiber with a core diameter of around 10 μm. This is because use of a multimode optical fiber having a large core diameter results in a high level of modal noise caused by intermode interference and time delay, which makes measurement of the speckle light intensity impossible. When an optical fiber with a core diameter in the neighborhood of 10 μm is used, however, the intensity of the light to be detected becomes weak so that in such cases it is advisable to carry out signal processing using the photon correlation method illustrated in FIGS. 12 and 13.

Figure 14A:
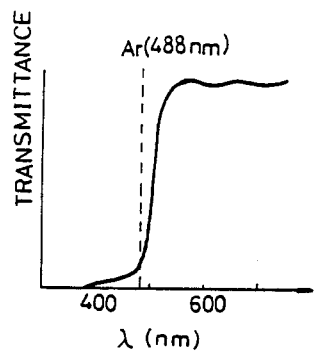
FIGS. 14(a) and 14(b) are characteristic curves showing the characteristics of other wavelength separation filters.
Figure 14B:
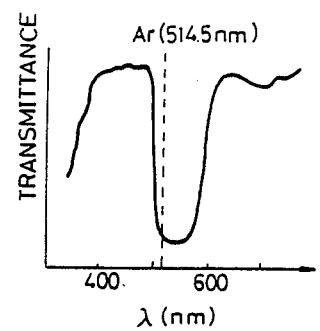

In the embodiments described above it is alternatively possible to use an Ar (argon) laser beam source. In this case, it is necessary for the wavelength separation mirror 15 and the wavelength separation filter 27 of FIG. 1 to have the characteristics shown in FIG. 14(a) of FIG. 14(b), depending on whether the wavelength of the beam source is 488 nm or 514.5 nm.

Figure 15:
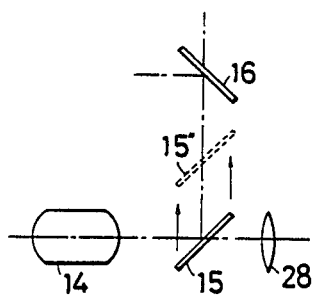
FIGS. 15 to 19 are schematic views of other optical system embodiments.

Another modification in the fundamental embodiment of FIG. 1 that can be made without any change in the effect obtained is that of replacing the swingable wavelength separation mirror 15 with one that changes position by vertical sliding as shown in FIG. 15.

Figure 16:
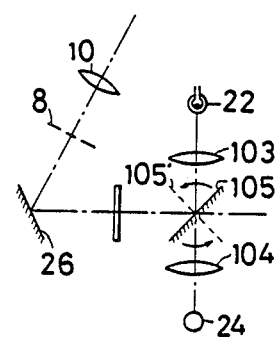

Further, as shown in FIG. 16, the observation light source 22 and the photographic light source 24 can be located on different light paths that meet at a mirror 105. More specifically, the observation light source 22 can be positioned on a path connecting with the mirror 105 via a condenser lens 103, while the photographic light source 24 can be positioned on a path connecting with the mirror 105 via a condenser lens 104. In this case, to enable both visual observation of the eye fundus and measurement of the state of eye fundus blood flow, the position of the mirror 105 is made switchable between the observation mode position shown by solid lines in FIG. 16 and a measurement mode position shown by a dashed line.

Figure 17:
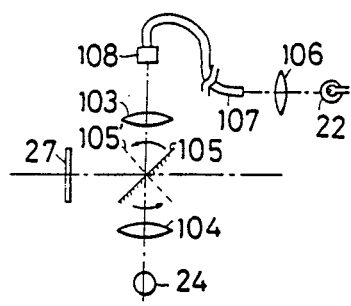
Figure 18:
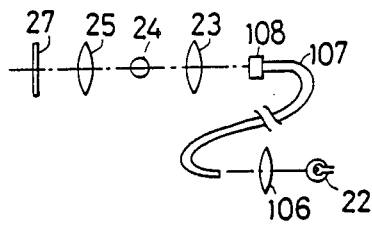

In a further variation shown in FIGS. 17 and 18, the light from the observation light source 22 is led to the condenser lens 103 via a condenser lens 106, an image fiber 107 and minute lens 108. In this case, if the fan for cooling the observation light source 22 and removing the heat produced thereby, which has conventionally been located in the main unit of the eye fundus camera, is relocated to some other location, it becomes possible to make the main unit of the apparatus according to this invention both more compact and lighter. Another merit of this arrangement is that the smaller design realizable by the removal of the fan from the main unit results in a unit that seems less intimidating to the person whose eye is being examined.

While in the embodiment shown in FIG. 1 the light quantity adjustment filter 2 is used for adjusting the quantity of the light passed into the optical system, if there is used a laser beam source which produces a linearly polarized laser beam and a polarizer is used as the filter 2, it becomes possible to adjust the laser beam light quantity by rotating the polarizer within a plane lying perpendicular to the light path. It is of cource possible to use a laser beam source which produces a linearly polarized laser beam and to carry out the adjustment of the light quantity using an ND (neutral density) filter or the like.

Figure 19:
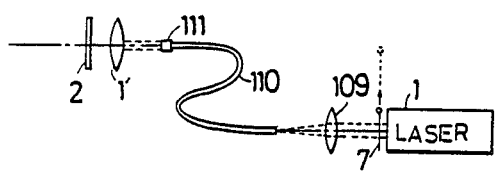

It is also possible, as shown in FIG. 19, to direct the light from the laser beam source 1 to the laser illuminating projector and to separate the laser beam source 1 from the main unit by passing the beam through a lens 109 into an optical fiber 110 and from the light-emitting end of the optical fiber through a minute lens 111 to the light quantity adjustment filter 2.

Figure 20:
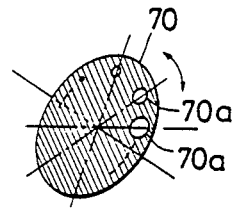
FIGS. 20 to 22 are perspective views of arrangements for varying the shape and/or size of the opening of a stop or a detection aperture.
Figure 21:
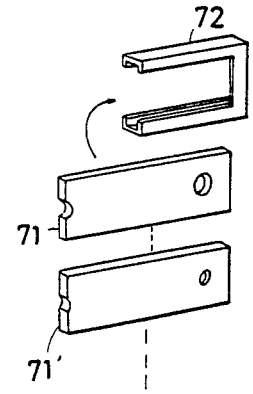
Figure 22:
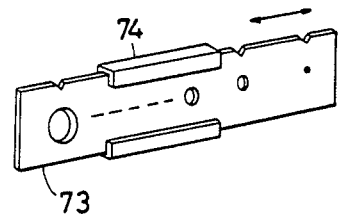

FIGS. 20 to 22 show various mechanisms for changing the sizes and shapes of the stops 5 and 6 (i.e. for changing the size and shape of the region illuminated by the laser beam) and also for changing the size and shape of the detection apertures 18 and 19.

FIG. 20 shows a circular disk 70 (which need not be circular but may instead be a sector-shaped or polygonal plate and is presumed to be circular here only to make the explanation simpler) which has a plurality of apertures 70a of desired sizes and shaped disposed along a circular locus having its center at the center of the disk. The circular disk 70 can be rotated about its center so as to select the particular aperture 70a of the desired shape and size.

FIG. 21 is a schematic view of a mechanism for varying the detecting apertures 18 and 19 and the stops 5 and 6, which consists of interchangeable members 71 and a retaining member 72. Each interchangeable member 71 is provided with an aperture of a given shape and size at such position that when the interchangeable member is inserted into the retaining member 72 is oriented so that the plane of the aperture will at this time lie perpendicular to the optical axis. Thus by selecting the one of a plurality of the interchangeable members 71, 71'... which has the aperture of the currently required size and shape and inserting it into retaining member, the size and shape of the detection apertures 18 and 19 or of the stops 5 and 6 can be varied as required.

FIG. 22 is a schematic view of a mechanism for varying the detection apertures 18 and 19 and the stops 5 and 6, which consists of a slide member 73 and a retaining member 74. The slide member 73 is provided with a plurality of apertures of various predetermined shapes and sizes so arranged that when the slide member 73 is inserted into the retaining member 74 it becomes possible to position the one of the apertures which is of the desired shape and size so as to intersect the optical axis with the plane of the aperture perpendicular to the optical axis. Thus by sliding the slide member 73 to select among the apertures of various shapes and sizes, it becomes possible to vary the detection apertures 18 and 19 and the stops 5 and 6.

The mechanism illustrated in FIGS. 20 to 22 can also be used as one way of varying the filter transmittance. More specifically, in any of the mechanisms in these figures the respective apertures can provided with ND filters each having a specific desired transmittance and the filter of the desired transmittance can be selected by moving it into the light path using the mechanism. In this case, the apertures are all of the same shape and size.

Figure 23:
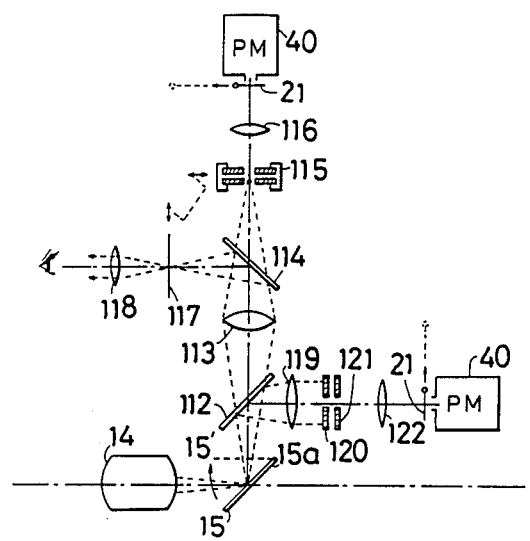
FIGS. 23 and 24 are schematic views of other embodiments of optical systems for measurement.

While in the method of detection employed in the fundamental embodiment described earlier the speckle pattern is detected at the Fraunhofer plane with respect to the object plane at which measurement is carried out, it is also possible to use an arrangement in which the speckle pattern is detected at the image plane. One example of an apparatus employing such an arrangement is shown in FIG. 23. In this embodiment, the speckle light reflected by the wavelength separation mirror 15 passes through a beam splitter 112, a condenser lens 113 and a beam splitter 114 to form an image on the image plane. Here only an image of the plane to be subjected to measurement formed solely by the alser beam is formed and the speckle pattern and this image are superposed. As the speckle pattern shifts with movement of the blood cells, the fluctuation in light intensity can be extracted though detection apaerture 115 and be detected by the photomultiplier 40 via a condenser lens 116. The signal processing can be carried out basically in the same way as in the fundamental embodiment. In this image plane detection method, while the entire region illuminated by the laser beam is formed as an image at the detection plane, since the detection aperture 115 is located at this plane, it becomes possible by selection of the position of the detection aperture 115 to sample, as the measurement region, specific portions of the region illuminated by the laser beam. In this respect, the method of this embodiment differs from the method of detection at the Fraunhofer diffraction plane. More specifically, differently from the case in which the detection is conducted at the Fraunhofer diffraction plane, the method according to this embodiment enables measurement of the blood flow at specific portions within the region illuminated by the laser beam. Also, since in line with the fundamental principle of optics whereby the image is formed by rays coming together at the image plane from various angles, the quantity of light is greater than that which can be detected at a single point at the diffraction plane. As a result, the measurement can be conducted with high sensitivity.

As described in the foregoing, the measurement region can be sampled by the detection aperture 115. Thus, to enable visual observation of the measurement region, the speckle light reflected by the beam splitter 114 is directed onto a reticle 117 located on an image plane equivalent to the plane of the detection aperture 115, where it forms an image which can be observed through an eyepiece 118. The reticle is provided with crosshairs, the intersection point of which consists with the center of the detection aperture 115. The reticle and the detection aperture 115 are mechanically linked so that the measurement position can be determined while observing the image thereof. The detection aperture 115 is constituted as a double aperture in order to enable adjustment of its shape and size. The position of its center is fixed.

The embodiment is further arranged so that the speckle light reflected by the beam splitter 112 advances through a condenser lens 119 to detection apertures 120 and 121 at which the fluctuation in light intensity is extracted, and then through a condenser lens 112 to the photomultiplier 40. As a result, it is also possible to carry out detection at the Fraunhofer diffraction plane in the same manner as in the fundamental embodiment.

As the apparatus for carrying out the present invention, there can be used either an apparatus capable of operating according to both the Fraunhofer diffraction plane detection method and the image plane detection method or an apparatus which operates solely according to the image plane detection method. The apparatus capable of operating according to both methods is particularly advantageous since it makes it possible to obtain complementary data, i.e. to obtain one set of data relating to the state of blood flow over the whole region illuminated by the laser beam and another set relating to the state of blood flow at a specific portion of the illuminated region.

Figure 24:
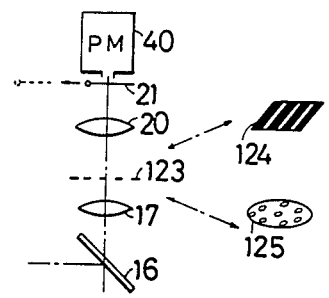

As an alternative to carrying out the measurement using the detection apertures 18 and 19 of FIG. 1 or the detection apertures 115, 120, and 121 of FIG. 23, it is possible as shown in FIG. 24 to conduct measurement of the state of blood flow using an optical spatial filter 123 disposed at the said Fraunhofer plane or image plane. When the conventional detection aperture is employed, the detection of the fluctuation in light intensity is in principle carried out with respect to the speckle pattern at a single point. In contrast, when a grating-type spatial filter or the like is used and the degree of movement of the speckle pattern in a given fixed direction is extracted, it is possible to detect from the speckle pattern movement frequency component a specific frequency which is determined by the grating pitch, and when this value is obtained through signal processing carried out by the signal processor 50, it becomes possible to obtain a measurement of the state of blood flow in a specific direction. On the other hand, where a random-pattern type spatial filter 125 is used, by extracting an irregular movement component of the speckle pattern movement and evaluating the frequency distribution of the so-obtained signal in accordance with the signal processing method shown in FIGS. 5 and 6, it becomes possible to obtain information regarding the irregularity of the state of blood flow. When the results of such measurements are evaluated together with the measurement results obtained in accordance with the fundamental embodiment of the invention, it become possible to obtain an even better understanding of the blood flow state under measurement, which is very advantageous in actual clinical applications.

The linkage of various adjustment mechanisms will now be explained.

In this invention, in order to prevent injury to the eye under examination by the laser beam, the intensity of the laser beam used for illumination of the eye being examined is set to comply with the various standards (IEC, ANSI) established to prevent such injury. While from a strictly technical point of view, this may be sufficient, it is further available to lower the psychological stress the patient is apt to feel when his or her eye is illuminated by laser light and, also, to reduce the unpleasant sensation of brightness produced by the laser light, by automatically setting the intensity of the laser beam used to illuminate the eye to a lower level during the stage of preparation for blood flow measurement than during the actual measurement. Further, it is a general characteristic of laser beam sources that their output is relatively instable immediately after the application of electric power. To avoid any adverse effect on the measurement by this instability, therefore, it is preferable to maintain the supply of electric power to the laser beam source 1 at all times. As, however, the laser beam is in fact unnecessary when the apparatus is being used as a fundus camera, it is preferable from the point of reducing psychological stress on the patient to arrange the apparatus such that during its use as a fundus camera no laser light reaches the eye being examined even though the laser beam source 1 is kept in the lasing state.

At the stage of preparing for carrying out measurement of the state of blood flow, it sometimes happens that a laser beam focal point is present at the center of the cornea 13a of the eye under examination. In this case, strong laser light is reflected in the direction of the photomultiplier 40 and if the photomultiplier 40 has high voltage applied thereto at this time, it may be damaged or at least have its service life shortened by the reception of the strong light. To prevent this, it is preferable for the photomultiplier to receive light only during the measurement of the state of blood flow.

In view of the foregoing considerations, the present invention provides the following interlinkage mechanisms.

Figure 25:
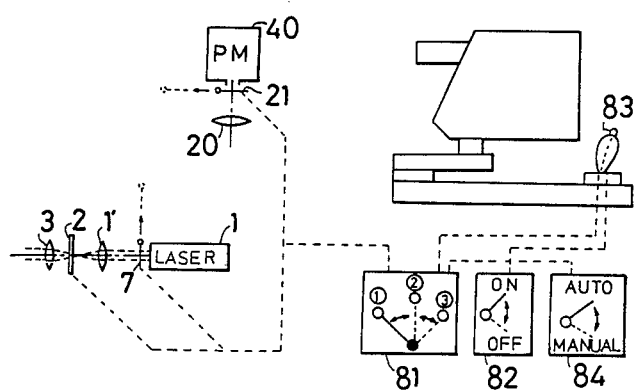
FIG. 25 is a schematic view of an arrangement for interlinking the operations of the apparatus components.

As shown in FIG. 25, the appartus according to this invention can function both as a fundus camera and as a blood flowmeter. To enable selection between these two types of operation, there is provided a switch 81 allowing selection among (1) mode for visual observation of measurement region, (2) mode for preparing for measurement of blood flow state, and (3) blood flow state measurement mode, which can be switched among either in the order of (1) —> (2) —> (3) or in the order of (3) —> (2) —> (1).

This arrangement is adopted in view of the problems inherent in prior art apparatuses. The apparatus is further provided with an eye fundus camera mode switch 82. In any of the modes (1), (2) and (3), when the switch 82 is turned on, the eye fundus camera functions enabling visual observation and photographing of the eye fundus are activated, while the laser beam source 1 stays in constant operation.

The apparatus is arranged to always be in the (1) mode at the time the main power switch is turned on. That is to say, even if the switch 81 should be set to mode (2) or (3), it is automatically reset to mode (1)

when the power is turned on. At this time, the laser beam from the laser beam source is cut off by the shutter 7 so that no laser light enters the eye under examination. Furthermore, the light-input face of the photomultiplier 40 is totally covered by the shutter 21.

When the function selection switch 81 is used to switch from mode (1) to mode (2), the shutter 21 of the photomultiplier 40 is left closed, the shutter 7 of the laser beam source 1 is opened, and the light quantity adjustment filter 2 is inserted into the light path, whereby a laser beam of lower intensity than that used during measurement of the blood flow state is directed into the eye under examination.

A joystick provided for focusing the eye fundus camera has a pushbutton switch 83 at the top. When the eye fundus camera mode switch is set to OFF, the pushbutton switch of the joystick is pressed, and the mode is changed from (2) to (3), the shutter 7 in front of the laser beam source 1 remains open, the light quantity adjustment filter 2 is switched so as to set the intensity of the laser beam for illuminating the eye under examination to the high level used during measurement of blood flow, and the shutter 21 is opened to enable detection of the speckle light by the photomultiplier 40.

After the elapse of a preset measurement period, the apparatus automatically assumes mode (2), the shutter 21 of the photomultiplier 40 closes, and the light quantity adjustment filter 2 is again switched to adjust the intensity of the laser beam to the level used during preparation for measurement, thereby lowering the level of the laser light directed into the eye under examination.

The apparatus is further provided with an AUTO/MANUAL switch 84 which is set to AUTO when the operator wants to have the measurement time set automatically and to MANUAL when he wants to set the measurement time at some arbitrarily chosen value. When the switch 84 is set to MANUAL with the eye fundus camera switch 82 OFF and the mode (2) selected, measurement can be begun by pushing the pushbutton switch 83 on the joystick once and be halted by pushing it a second time.

When in any of the modes (1), (2) or (3), it is possible to carry out eye fundus photography by setting the eye fundus camera switch 82 to ON and pressing the pushbutton switch 83 on the joystick. By this method, it is possible to carry out the operation simply and safely.

Further, it is possible to mechanically link the detection apertures 18 and 19 with the stops 5 and 6 (FIG. 1) by means of wires or the like in such manner that once the region of laser beam illumination has been set by the stops 5 and 6, the size and shape of the detection apertures 18 and 19 will be automatically selected.

One merit of the embodiments described in the foregoing is that since they use lasers that produce visible light, the operator is able to carry out various observations directly with his own eyes and, specifically, during visual observation of the eye fundus is able to visually confirm the region of the eye fundus illuminated by the laser beam, so that it is unnecessary to provide any special detection or display devices for use in observing the fundus of the eye under examination.

In this connection, however, when a normal human eye senses visible light, the pupi of the eye contracts in proportion to the amount of light falling thereon per unit time. When the pupil contracts, because of the geometry of the optical system, it is difficult to direct the laser beam from the laser beam source onto the eye fundus. Even if the laser beam should be successfully directed onto the eye fundus, the resulting miosis would prevent almost all of the light scattered by the blood cells within the eye fundus blood vessels from finding its way back out of the eye, preventing the photomultiplier from detecting speckle light and making measurement impossible. It therefore becomes necessary to use a mydriatic, which leads to considerable discomfort for the patient since it causes a forced dilation of the pupil which would under natural circumstances contract to protect the retina when subjected to the laser illumination. As a result, the patient experiences unpleasant brightness. Moreover, the effect of the mydriatic persists even after the measurement of the blood flow state has been completed and the patient's vision will not return to normal until the effect of the medication has worn off.

Further, where the patient is suffering from some illness which makes it advisable not to administer a mydriatic, it will be difficult if not impossible to measure the blood flow state at the eye fundus.

FIG. 26 shows an embodiment of the invention which overcomes these problems.

Figure 27:
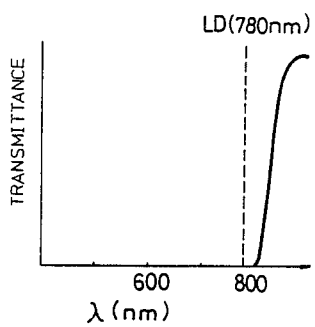
FIGS. 27 to 29 are characteristic curves representing optical characteristics of filters.
Figure 28:
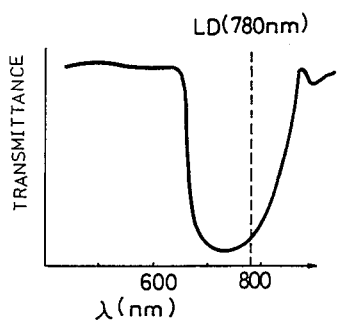

The apparatus illustrated in FIG. 26 is designed for carrying out measurement of blood flow state while also being provided with the function of an eye fundus camera that does not require use of a mydriatic. In this apparatus, the light produced by an observation light source 201 passes through a condenser lens 202, a filter 203, a beam splitter (or half mirror) 204 and a condenser lens 205, whereafter it is reflected by a mirror 206. The filter 203 exhibits the spectral characteristics shown in FIG. 27 so as to cut any wavelength components of the observation light equal to or shorter than the wavelength of the laser beam produced by a semiconductor laser 200 (to be described later). The apparatus is further provided with a photographic light source 207, the light from which passes through a condenser lens 208 and a wavelength separation filter 209 exhibiting the spectral characteristics shown by FIG. 28, whereafter it is reflected by the beam splitter (or half mirror) 204, passes thorugh the condenser lens 205 and is reflected by the mirror 206. The portion of the light of the photographic light source 207 that transmits through the beam splitter (or half mirror) 204 and the portion of the observation light that is reflected by the same are absorbed by a light trap 210. The observation light and photographic light reflected by the mirror 206 advance through a ring slit 211 and relay lenses 212 and 213 to be reflected by a ring mirror 214 and thereafter pass through an objective lens 215 to be once converged in a ring shape on the cornea 13a of the eye under examination 13, and then advance as diverged to reach and illuminate the eye fundus 13b.

The laser beam from the semiconductor laser beam source 200 passes through a condenser lens 216 and then through a light quantity adjustment filter 217 for adjusting the light intensity. It then advances through relay lenses 218 and 219 and is guided into the eye fundus illuminating projector of the eye fundus camera. Further, between the relay lenses 218 and 219 there are disposed stops 220 and 221 for enabling selection of the size and shape of the region of the eye fundus illuminated by the laser beam. The laser light exiting from the relay lens 219 is reflected by a prism 222 disposed at one part of the annular opening of the ring slit 211 and thereafter passes along the same light path to the eye fundus as that followed by the eye fundus observation and photographic light beams. As a result, the laser beam passes through the relay lenses 212 and 213, is reflected by the ring mirror 214, passes through the objective lens 215, converges in a ring shape on the cornea 13a of the eye under examination 13, and then advances as diverged to reach and illuminate a region of the eye fundus 13b which is large in comparison with the diameter of the eye fundus blood vessels. As the path of the laser beam coincides with that of the observation and photographic light beam, the laser beam can be made to impinge on the desired region of the eye fundus 13b by use of the mechanisms for swinging the eye fundus camera vertically and horizontally and also by use of the eye fixation mechanism.

Figure 29:
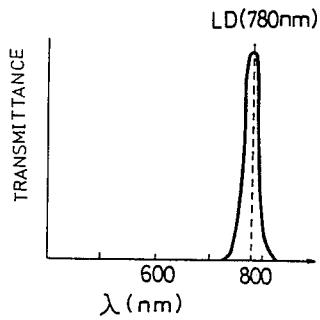

The speckle light produced when the laser beam is scattered by the blood cells moving through the eye fundus blood vessels and also the reflected observation and photographic light are all received again by the objective lens 15 and then advance through the ring mirror 214 and a photographic lens 223 to a beam splitter (or half mirror) 224, from where the light path is split in two. The light reflected by the beam splitter (or half mirror) 224 advances through a relay lens 225, an interference filter 226, detection apertures 227 and 227, and a lens 229 to a photomultiplier 40 where it is detected. As the interference filter 226 has the spectral characteristics shown in FIG. 29, it passes only light within the wavelength range of that generated by the semiconductor laser 200. Thus, by the action of the filters 203 and 209 and the interference filter 226, the speckle light produced by the laser light from the semiconductor laser beam source is separated from the observation and photograhic light so that only the speckly light is detected by the photomulitplier 40. The observation light and speckle light which transmit through the beam splitter (or half mirror) 224 pass through a relay lens 230, is reflected by a swingable mirror 231, whereafter it advances through a relay lens 232, are reflected by a mirror 233 and then pass through an infrared TV camera lens into an infrared TV camera 240 where they are detected. An image of the eye fundus is displayed on a TV monitor 241. Observation can be carried out simultaneously with measurement, and, if desired, the photographic light from the photographic light source 207 can be used to record a photographic image of the eye fundus on photographic film 235. Moreover, the video signal representing the eye fundus output by the infrared TV camera 240 is set through a camera controller 242 to be stored in a frame memory 243. Further, if necessary, reproduction, processing and other operations can be carried out on the stored video data using a signal processor 50.

As the observation of the eye fundus is carried out using light in the infrared band, the region illuminated by the laser beam from the semiconductor laser appears in the image fundus image seen on the TV monitor 241, making it possible to confirm the measurement position.

It goes without saying that the modifications shown in FIGS. 11 to 24 can also be applied to the embodiment illustrated in FIG. 26.

The embodiment of FIG. 26 provides the following advantages effects:

(a) Since neither the observation light nor the laser beam used for measurement are in the visible light band, the patient experiences no brightness.

(b) Since neither the observation light nor the laser beam used for measurement are in the visible light band, there is no need to use a mydriatic, which results in less stress on the patient.

(c) As there is no need to dilate the pupil, there is no need to take into consideration the effect that use of a mydriatic might have on any afflication the patient may be suffering.

(d) As the state of eye fundus blood flow can be measured not only when the pupil is dilated but also when it is not, no need arises to investigate what effect the use of a mydriatic has on the state of blood flow.

Moreover, when a semiconductor laser is used as the laser beam source, the following additional effects can be obtained:

(e) As a semiconductor laser is small and light in weight, it is possible to realize a more compact and lighter apparatus.

(f) As semiconductor lasers are inexpensive, the cost of the apparatus can be reduced.

Figure 13:
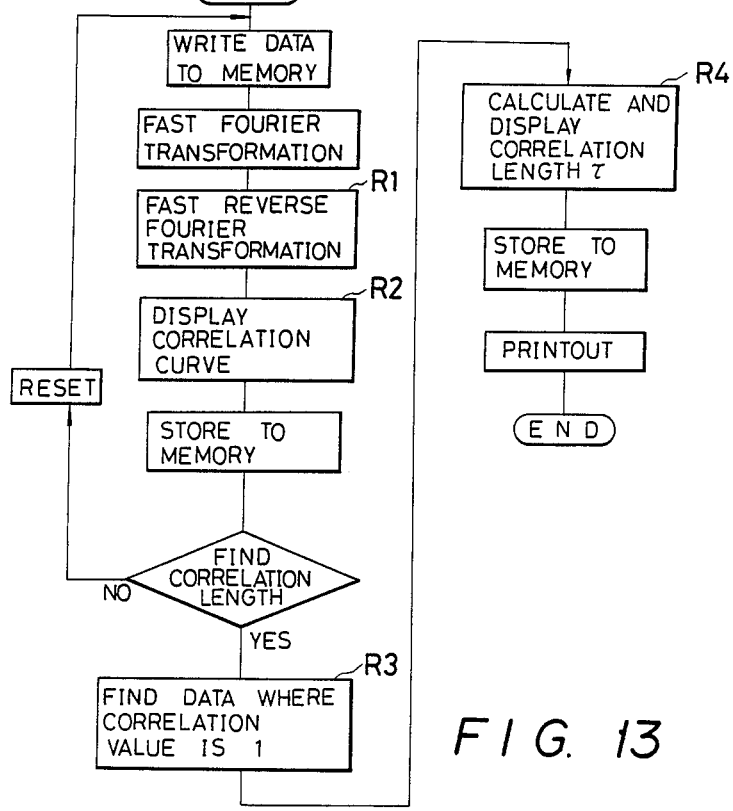
Figure 30:
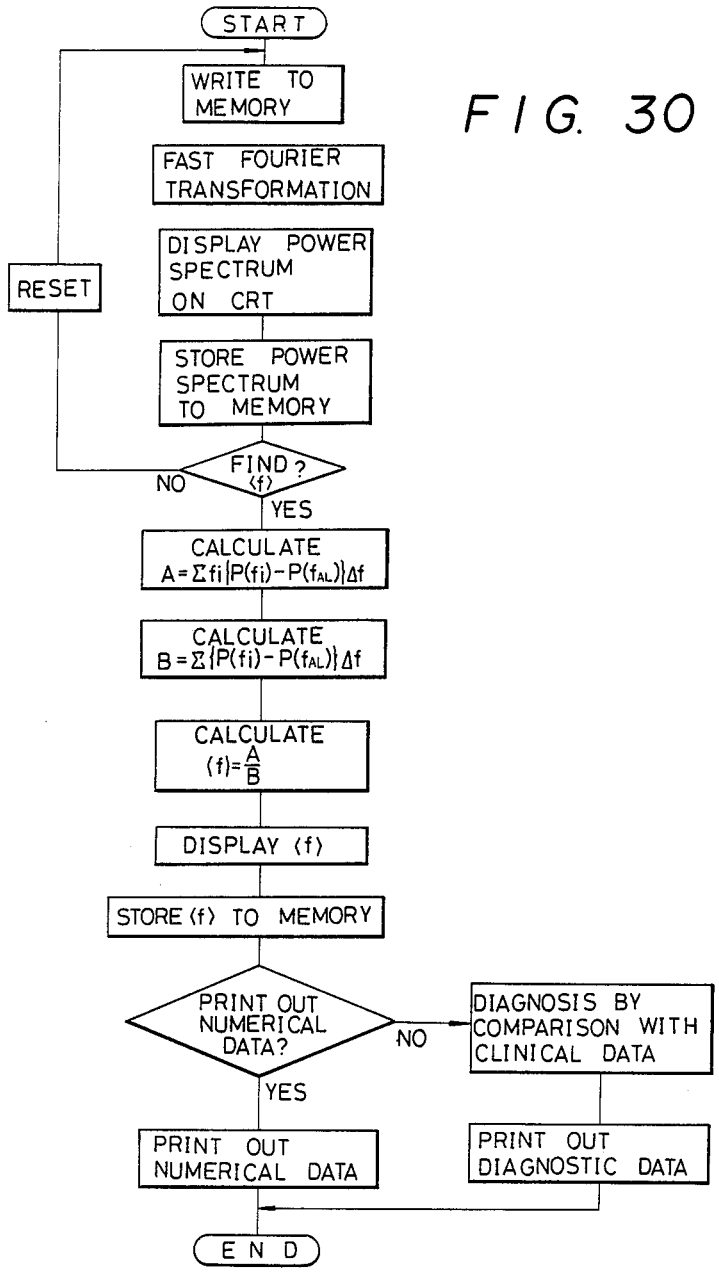
FIG. 30 is a flowchart showing another method of evaluation of speckle patterns.

While procedures for evaluating the speckle signal have been explained with reference to FIGS. 6 and 13, it is also possible to carry out the evaluation on the basis of the differential mean frequency defined by the following equation:

$$<f_A> = \frac{\int_{f_{AL}}^{f_{AH}} f(P(f) - P(f_{AL}))df}{\int_{f_{AL}}^{f_{AH}} (P(f) - P(f_{AL}))df}$$

where f is the frequency, P(f) the power spectrum, $f_{AL}$ the lowest frequency within the signal analysis band and $f_{AH}$ the highest frequency within the signal anylysis band. The calculation is conducted for example in accordance with the flowchart shown in FIG. 30 and the result is output to the printer 65 (FIG. 4).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmological diagnosis method comprising the steps of illuminating a region of the eye with a laser beam of prescribed diameter to produce a laser speckle pattern formed by light scattered by blood cells within the tissue of the eye, detecting movement of the laser speckle pattern as fluctuation in the light intensity of the speckles at an observation point and producing a speckle signal corresponding to the detected movement, obtaining the power spectrum distribution of the speckle signal, evaluating the power spectrum distribution configuration from the results of a calculation of the mean frequency thereof and determining the blood flow state in the tissue from the results of the evaluation.

2. An ophthalmological diagnosis method according to claim 1, wherein observation and photographic light beams follow the same light path as the laser beam.

3. An ophthalmological diagnosis method according to claim 1, wherein the wavelength region of the laser beam and that of the observation and photographic light beams are determined so as to make the beams separable.

4. An ophthalmological diagnosis method according to claim 1, wherein the laser light, observation light and illumination light reflected from the eye tissue are received via the same light-receiving optical system and the laser light alone is selectively extracted therefrom.

5. An ophthalmological diagnosis method according to claim 1, wherein said prescribed diameter is set to be larger than the diameter of blood vessels within said tissue.

6. An ophthalmological diagnosis method according to claim 5, wherein said prescribed diameter is changeable in steps.

7. An ophthalmological diagnosis method according to claim 1, wherein, defining the surface of the tissue as the object surface, the movement of a diffraction speckle pattern is detected asa fluctuation in light intensity observed at the Fraunhofer diffraction plane with respect to the object plane.

8. An ophthalmological diagnosis method according to claim 1, wherein the laser speckles are detected at the observation point by use of at least one detection aperture which is variable in size and shape.

9. An ophthalmological diagnosis method according to claim 1, wherein the logarithm of the power spectrum is used for calculation of the mean frequency.

10. An ophthalmological diagnosis method according to claim 1, wherein the shape of the region illuminated by the laser beam is adjustable.

11. An ophthalmological diagnosis method according to claim 1, wherein the shape of the detection aperture is adjustable.

12. An ophthalmological diagnosis method according to claim 1, wherein the speckle pattern can be visually observed.

13. An ophthalmological diagnosis method according to claim 1, wherein the movement of an image plane speckle pattern observed at an image plane which is the conjugate of the tissue of the eye being examined is detected as fluctuation in light intensity.

14. An ophthalmological diagnosis method according to claim 1, wherein the speckle pattern is detected as fluctuation in light intensity both at the image plane and at the Fraunhofer diffraction plane.

15. An ophthalmological diagnosis method according to claim 14, wherein a spatial filter is disposed at one or both of the Fraunhofer plane and the image plane in place of a detection aperture.

16. An ophthalmological diagnosis method according to claim 1, wherein the laser beam used is light of a wavelength in the near infrared band.

17. An ophthalmological diagnosis method according to claim 1, wherein the observation light used has a wavelength in the near infrared band.

18. An ophthalmological diagnosis method according to claim 17, wherein an interference filter which passes light only in the wavelength band of the laser light is inserted in front of the speckle detection aperture, a filter which passes only light of wavelengths longer than the wavelength of the laser light is inserted in front of the observation light source, and a filter which passes only light of wavelength outside the wavelength band of the laser light is inserted in front of the photographic light source.

19. An ophthalmological diagnosis method comprising the steps of illuminating a region of the eye with a laser beam of prescribed diameter to produce a laser speckle pattern formed by light scattered by blood cells within the tissue of the eye, conducting a photon count with respect to the speckle light at an observation point, determining the photon probability distribution on the basis of the photon count, using the photon probability distribution for detecting movement of the laser speckle pattern as fluctuation in light intensity of the speckles, producing a speckle signal corresponsding to the detected movement, subjecting the speckle signal to photon correlation processing to obtain a photon correlation curve, and determining the state of blood flow from the photon correlation curve.

20. An ophthalmological diagnosis apparatus comprising:
   a laser beam source;
   a laser beam optical system for guiding laser light from the laser beam source, adjusting it to a predetermined beam diameter and causing it to illuminate a region of eye tissue of predetermined area;
   means for measuring light scattered from the illuminated region of eye tissue and producing a signal corresponding to the result of the measurement; and
   means for producing the signal from the measuring means;
   wherein movement of a laser speckle pattern produced by the scattered light is detected as fluctuation in intensity of the speckle light, the detected movement is converted into a speckle signal, the speckle signal is processed to determine at least one of the configuration of the power spectrum distribution of the speckle signal and the photon correlation curve of the speckle signal, and determining the state of blood flow from the result obtained by processing the speckle signal.

21. An ophthalmological diagnosis apparatus according to claim 20, further comprising optical systems for visual and photographic observation of the region of eye tissue, which optical systems share the optical path of the laser beam optical system.

22. An ophthalmological diagnosis apparatus according to claim 21, wherein the optical systems for visual and photographic observation of the region of the eye tissue have separate light sources disposed on different optical axes.

23. An ophthalmological diagnosis apparatus according to claim 22, wherein the observation light source is separated from the apparatus proper and is connected therewith by an optical fiber.

24. An ophthalmological diagnosis apparatus according to claim 23, wherein the means for detecting the speckle light is a photodetector separated from the apparatus proper and connected therewith by an optical fiber.

25. An ophthalmological diagnosis apparatus according to claim 20, wherein the laser beam source is an He-Ne laser or an argon laser.

26. An ophthalmological diagnosis apparatus according to claim 20, further comprising a wavelength separation mirror which reflects only the laser speckle light component of the scattered light.

27. An ophthalmological diagnosis apparatus according to claim 26, wherein the wavelength separation mirror is swingably or slidably mounted to be insertable into and removable from the light path.

28. An ophthalmological diagnosis apparatus according to claim 20, wherein the measurement means has at least one detection aperture for detection of the speckle pattern.

29. An ophthalmological diagnosis apparatus according to claim 28, wherein the detection aperture is disposed at a plane which, when the plane of the eye tissue to be observed is defined as the object plane, falls at the Fraunhofer diffraction plane with respect to the object plane.

30. An ophthalmological diagnosis apparatus according to claim 29, wherein the size and shape of the detection aperture is adjustable.

31. An ophthalmological diagnosis apparatus according to claim 28, wherein the detection aperture is disposed at the conjugate image plane with respect to the eye tissue plane and image plane speckles are detected.

32. An ophthalmological diagnosis apparatus according to claim 31, further comprising a mechanism for visually observing and adjusting the position of the detection aperture disposed at the image plane.

33. An ophthalmological diagnosis apparatus according to claim 32, wherein the visual observation and adjustment is carried out using an reticle linked with the detection aperture.

34. An ophthalmological diagnosis apparatus according to claim 28, wherein a detection aperture is disposed at each of the image plane and the Fraunhofer detection plane.

35. An ophthalmological diagnosis apparatus according to claim 20, further comprising at least one stop mechanism for adjusting the size and shape of the region illuminated by the laser beam.

36. An ophthalmological diagnosis apparatus according to claim 35, further comprising a mechanism for adjusting the size of the detection aperture in an interlinked relationship with the adjustment of the stop mechanism.

37. An ophthalmological diagnosis apparatus according to claim 20, wherein the quantity of light entering the laser optical system from the laser beam source is adjustable.

38. An ophthalmological diagnosis apparatus according to claim 37, wherein the adjustment of the quantity of light is conducted using a light quantity adjustment filter or a polarizer.

39. An ophthalmological diagnosis apparatus according to claim 38, wherein the adjustment of the quantity of light is linked with a switch for initiating measurement.

40. An ophthalmological diagnosis apparatus according to claim 20, wherein the laser source is separated from the apparatus proper and is connected therewith by an optical fiber.

41. An ophthalmological diagnosis apparatus according to claim 20, wherein the laser speckle pattern can be visually observed.

42. An ophthalmological diagnosis apparatus according to claim 20, wherein the laser light and the observation light are beams with wavelength spectra in the near infrared band.

43. An ophthalmological diagnosis apparatus according to claim 42, wherein an interference filter which passes light only in the wavelength band of the laser light is inserted in front of the speckle detection aperture, a filter which passes only light of wavelengths longer than the wavelength of the laser light is inserted in front of the observation light source, and a filter which passes only light of wavelengths outside the wavelength band of the laser light is inserted in front of the photographic light source.

44. An ophthalmological diagnosis apparatus according to claim 42, further provided with a device for monitoring the eye fundus image and the laser-illuminated region.

45. An ophthalmological diagnosis apparatus according to claim 44, further comprising a memory for storing the information displayed by the monitor device.

46. An ophthalmological diagnosis apparatus according to claim 42, arranged to function as an eye fundus camera not requiring adminstration of a mydriatic.

* * * * *